US012751675B2

(12) United States Patent
Van Gastel et al.

(10) Patent No.: US 12,751,675 B2
(45) Date of Patent: Oct. 6, 2026

(54) MRI SYSTEM, IN PARTICULAR A METHOD AND SYSTEM FOR GENERATING A CARDIAC TRIGGER SIGNAL

(71) Applicant: KONINKLIJKE PHILIPS N.V., Eindhoven (NL)

(72) Inventors: Mark Josephus Henricus Van Gastel, Tilburg (NL); Willem Verkruijsse, Veldhoven (NL); Daniel Wirtz, Hamburg (DE); Christoph Günther Leussler, Hamburg (DE); Maria Estrella Mena Benito, Eindhvoven (NL); Julien Thomas Senegas, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 336 days.

(21) Appl. No.: 18/274,478

(22) PCT Filed: Jan. 13, 2022

(86) PCT No.: PCT/EP2022/050600

§ 371 (c)(1),
(2) Date: Jul. 27, 2023

(87) PCT Pub. No.: WO2022/161775

PCT Pub. Date: Aug. 4, 2022

(65) Prior Publication Data

US 2024/0164729 A1 May 23, 2024

(30) Foreign Application Priority Data

Jan. 28, 2021 (EP) .................................... 21154061

(51) Int. Cl.
*A61B 5/00* (2006.01)
*A61B 5/0245* (2006.01)
(Continued)

(52) U.S. Cl.
CPC .......... *A61B 5/7285* (2013.01); *A61B 5/0062* (2013.01); *A61B 5/0245* (2013.01);
(Continued)

(58) Field of Classification Search
CPC ... A61B 5/7285; A61B 5/0062; A61B 5/0245; A61B 5/055
See application file for complete search history.

(56) References Cited

U.S. PATENT DOCUMENTS 6,188,482 B1 2/2001 Cloud
7,128,714 B1 10/2006 Antonelli et al.
(Continued)

FOREIGN PATENT DOCUMENTS

EP 1623667 A1 2/2006
WO 2013185936 A1 12/2013
WO 2013185937 A1 12/2013

OTHER PUBLICATIONS

Verkruysse et al, Remote plethysmographic imaging using ambient light, Optics Express (2008).
(Continued)

*Primary Examiner* — Joel F Brutus

(57) ABSTRACT

A system provides a trigger signal for controlling the operation of a scanner. A laser speckle vibrometry system is used for non-contact vibration sensing. A patient coil arrangement is provided for mounting adjacent (e.g. fixing to) a body of a patient and it comprises at least one window enabling passage of the laser light of the optical system to the body of the patient. The detected reflected laser light (through the window) is processed to detect the cardiac cycle and to generate a cardiac trigger signal for the control of the scanner.

13 Claims, 10 Drawing Sheets

(51) Int. Cl.
*A61B 5/055* (2006.01)
*G01H 9/00* (2006.01)

(52) U.S. Cl.
CPC ............ *A61B 5/055* (2013.01); *G01H 9/004* (2013.01); *A61B 2560/0223* (2013.01)

(56) References Cited

U.S. PATENT DOCUMENTS

| | | | | |
|---|---|---|---|---|
| 7,925,056 | B2 | 4/2011 | Presura et al. | |
| 10,240,912 | B2 | 3/2019 | Muijs et al. | |
| 2003/0095263 | A1 | 5/2003 | Varshneya et al. | |
| 2005/0122108 | A1 * | 6/2005 | Yasuhara ............ | G01R 33/341 324/318 |
| 2010/0226543 | A1 | 9/2010 | Zalevsky | |
| 2011/0230738 | A1 | 9/2011 | Chance | |
| 2013/0063148 | A1 * | 3/2013 | Ma .................. | G01R 33/34023 324/318 |
| 2014/0073902 | A1 * | 3/2014 | Popescu ................ | A61B 6/541 600/407 |
| 2016/0066790 | A1 | 3/2016 | Shcherbakov et al. | |
| 2016/0331239 | A1 | 11/2016 | MacLaren et al. | |
| 2017/0143271 | A1 * | 5/2017 | Gustafsson ............ | A61B 5/055 |
| 2020/0046300 | A1 | 2/2020 | Senegas et al. | |
| 2020/0077030 | A1 * | 3/2020 | Asukabe ................ | H04N 23/75 |
| 2020/0302619 | A1 * | 9/2020 | Lu .......................... | G06T 7/521 |

OTHER PUBLICATIONS

Martinek, Radek, et al. "A Low-Cost System for Seismocardiography-Based Cardiac Triggering: A Practical Solution for Cardiovascular Magnetic Resonance Imaging at 3 Tesla." IEEE Access 7 (2019): 118608-118629.
International Search Report and Written Opinion from PCT/EP2022/050600 mailed Apr. 21, 2022.
Scalise et al "Non-Contact Cardiac Monitoring from Carotid Artery using Optical Vibrocardiography Medical Engineering & Physics" vol. 30, No. 4, May 2008.
Scalise et al "A Laser Doppler Approach to Cardiac Motion Monitoring: Effects of Surface and Measurement Position" L Proc. SPIE 6345, Seventh International Conference on Vibration Measurements by Laser Techniques: Advances and Applications, 63450D (Jun. 21, 2006); doi: 10.1117/12.693151.
Iannuzzelli et al "Approaches to MRI Gating using Multiple Sensors" Johns Hopkins APL Technical Digest, vol. 20, No. 2, (1999).
Beiderman et al "Remote Estimation of Blood Pulse Pressure via Temporal Tracking of Reflected Secondary Speckles Pattern" Journal of Biomedical Optics 15(6) Nov./Dec. 2010.
Sirevaag et a "Cardiorespiratory Interactions: Noncontact Assessment using Laser Doppler Vibrometry" Psychophysiology 53 (2016) p. 847-867.
Ul'yanov et al "Speckle Interferometry for Biotissue Vibration Measurement" Optical Engineering 33(3) p. 908-914 (1994).
MacLaren et al "Contact-free Physiological Monitoring using a Markerless Optical System" Magnetic Reson. in Med. vol. 74, No. 1, pp. 571-577.

* cited by examiner

MRI SYSTEM, IN PARTICULAR A METHOD AND SYSTEM FOR GENERATING A CARDIAC TRIGGER SIGNAL

CROSS REFERENCE TO RELATED APPLICATIONS

This application is a U.S. national phase application of International Application No. PCT/EP2022/050600 filed on Jan. 13, 2022, which claims the benefit of EP Application Ser. No. 21/154,061.2 filed on Jan. 28, 2021 and is incorporated herein by reference.

FIELD OF THE INVENTION

The invention relates to magnetic resonance imagining, MRI, systems, and in particular the timing of operation of the MRI system using a cardiac trigger signal.

BACKGROUND OF THE INVENTION

Magnetic resonance imaging (MRI) is a medical imaging technique used in radiology to form pictures of the anatomy and the physiological processes of the body. MRI scanners use strong magnetic fields, magnetic field gradients, and radio waves to generate images of the organs in the body.

MRI is widely used in hospitals and clinics for medical diagnosis and staging and follow-up of disease without exposing the body to radiation. MRI is based on the ability of certain atomic nuclei to absorb radio frequency energy when placed in an external magnetic field. The resultant evolving spin polarization can induce an RF signal in a radio frequency coil and thereby be detected.

Hydrogen atoms are most often used to generate a macroscopic polarization that is detected by antennas close to the subject being examined. Hydrogen atoms are naturally abundant in humans and other biological organisms, particularly in water and fat. For this reason, most MRI scans essentially map the location of water and fat in the body.

Pulses of radio waves excite the nuclear spin energy transition, and magnetic field gradients localize the polarization in space. By varying the parameters of the pulse sequence, different contrasts may be generated between tissues based on the relaxation properties of the hydrogen atoms therein.

Cardiac magnetic resonance imaging methods have been of limited clinical value for several reasons. The heart is a moving object and is hence particularly difficult to image, especially if an imaging plane is set in space with the heart moving in and out of the imaging plane. The breathing of the examined patient also causes a periodic motion of the heart and other surrounding internal structures of the body of the examined patient. The imaging situation is further complicated by the beating motion of the heart itself which is added to the breathing motion. Both motions, heart motion and breathing motion, are present during the relatively long period of acquisition of MR signals and cause undesirable artefacts in the resulting images. Image quality may be degraded because of motion blurring for example.

Trigger signals (e.g. from an ECG or PPG) are commonly used to gate the acquisition of medical imaging data either to mitigate the effect of heart motion or to capture images which are resolved relative to the motion phase of the heart. High quality triggering in medical imaging, especially in magnetic resonance imaging, is vital for a large number of examinations, not only for cardiac imaging, for example also for abdominal or pelvis imaging.

For cardiac imaging, only with good quality trigger signals the imaging sequence can be carried out at equal expiration states or equal points during the cardiac cycle resulting in superior image quality.

With ECG gating, ECG signals are used to determine the heartbeat and therewith trigger the imaging device. However, this method has several disadvantages. First, the ECG signal is distorted during the MRI scan due to the magneto-hydrodynamic effect to radiofrequency, and to magnetic field gradient switching. Furthermore, the use of ECG also requires more patient preparation time (to mount the electrodes, connect and activate the wireless transmitter etc.) and it is not able to determine the motion of the heart.

A recent alternative is the use of wearable patient monitoring device capable of recording the heart rate, blood oxygen saturation, surface temperature and humidity during magnetic resonance imaging. Peripheral Pulse Unit (PPU) sensors are for example often used that detect the heart beat using PPG integrated in a finger-clip. A shortcoming of using this method is that the physiological delay between the actual heart beat and the resulting effect in the extremities has to be taken into account, and additional scanning for delay determination has to be done. Moreover, this method is not very reliable in arrhythmic patients.

Camera-based techniques have also been proposed, e.g. by using an optical camera and tracking of body motion induced by cardiac contractions. In rPPG (remote photoplethysmography) the color blush in the patient's face is imaged and the heart rhythm is calculated from the cardiac induced color changes in the video. Again, the physiological delay has to be taken into account as well as the fact that cardiac signals in real-time cannot yet be deduced since the computing time necessary for signal extraction is too long. Moreover this method can only be applied when some patches of skin are visible to a camera in, or close to, the MRI bore.

US 2014/073902 discloses non-contact sensing using analysis of an optical speckle pattern obtained by focusing light on a skin region above an artery.

Julian Maclaren et. al. "Contact-free physiological monitoring using a markerless optical system", Magnetic Resonance in Medicine, vol. 74, no. 2, pp. 571-577, XP055291027 discloses the combination remote PPG (rPPG) and motion analysis for cardiac and respiratory monitoring, respectively.

There is a need for an improved system for generating trigger signals, synchronized with the movement of a body to be imaged.

SUMMARY OF THE INVENTION

The invention is defined by the claims.

According to examples in accordance with an aspect of the invention, there is provided a system for providing a trigger signal for controlling the operation of a scanner, comprising:

- a laser speckle vibrometry system for non-contact vibration sensing, comprising a laser for delivering laser light and an optical detector for detecting reflected laser light; and
- a patient coil arrangement for mounting against a body of a patient, comprising at least one window enabling the passage of the laser light to the body of the patient;
- a mounting arrangement for mounting the laser such that the delivered laser light passes through the window; and a controller which is adapted to process the detected reflected laser light to detect the cardiac cycle and to generate a cardiac trigger signal for the control of the scanner.

This system generates a trigger signal suitable for MR-compatible heart motion tracking or tracking of motion of other bodies to be imaged. It makes use of non-contact vibration sensing, in particular laser speckle vibrometry. It is used for cardiac triggering.

Laser speckle vibrometry does not rely on the Doppler principle. A laser speckle vibrometry system may be implemented at low cost with fewer components than for example a laser Doppler system, and can be integrated into a smaller space. Imaging may also be performed by adapting the lens focus used with the 2D image sensor.

The system can be easily integrated into scanners such as MRI scanners, in that it is designed as part of a patient coil arrangement. Compared to camera-based PPG, there is no requirement on skin visibility, there is no physiological delay and it allows near real-time processing. High-resolution (triggered) MR-imaging is thereby possible without additional on-body sensors or workflow impairments.

The optical system is for example mounted outside the patient coil and thereby does not adversely affect the collection of RF signals by the patient coil. The mounting arrangement aligns the laser output with the body of the patient, either along a direct line of sight or additionally incorporating mirrors.

The optical system is example defocused at the distance of the body surface.

In a first set of examples, the laser is mounted remote from the patient coil and the output of the laser is directed to the window. Thus, any magnetic interference between the optical system and the scanner hardware is reduced to a minimum.

In a second set of examples, the laser is mounted remote from the patient coil and the output of the laser is directed to a mirror which is mounted at the window. This assists in providing alignment of the laser light with the window.

In a third set of examples, the laser and optical detector are mounted on a handle which has an adjustable position relative to the body. This enables simple positional adjustment to obtain the desired alignment of the optical system with the patient coil window.

In a fourth set of examples, the laser and optical detector are mounted on the patient coil arrangement. In this way, there is automatic alignment between the optical system and the window. The laser and optical detector, if MRI compatible, may even be within the structure of the patient coil so that the window is only present in the patient facing side of the patient coil. A coil support may be provided for decoupling movement of the body from movement of the patient coil arrangement so that the optical system does not move with the patient.

In all examples, the system may comprise a plurality of lasers and associated optical detectors, with different lasers directed to different locations of the body. This gives an improved signal to noise ratio. The different locations are for example different locations of the chest of a patient.

The system may further comprise a calibration system for calibrating an amount of defocus of the optical detector based on detected chest movements. Thus, the optical sensing may be calibrated to provide the best signal for a particular patient.

The system may further comprise a tracking system for tracking movement of the patient coil arrangement and for adjusting the direction of the laser light to the at least one window in dependence on the tracked movement. The movement of the patient coil arrangement may be caused by movement of a patient support (e.g. bed) or movement of the patient (e.g. respiration).

The system is for example for providing a trigger signal for controlling the operation of an MRI scanner, for example for cardiac MRI.

The invention also provides an MRI scanner comprising:

a patient support;

a superconducting magnet;

a gradient coil;

an RF transmit coil; and the system defined above for generating a trigger signal for controlling the scanner.

The invention also provides a method for providing a trigger signal for controlling the operation of a scanner, comprising:

controlling a laser to deliver laser light through a window of a patient coil arrangement to the body of a patient;

receiving a signal representing detected reflected laser light;

processing the signal representing the detected reflected laser light thereby to implement laser speckle vibrometry to perform non-contact vibration sensing to detect the cardiac cycle; and generating a cardiac trigger signal for the control of the scanner.

The method may further comprise tracking movement of the patient coil arrangement and adjusting the direction of the laser light to the window in dependence on the tracked movement.

The invention also provides a system for providing a trigger signal for controlling the operation of a scanner, comprising:

a laser speckle vibrometry system for non-contact vibration sensing, comprising a laser for delivering laser light and an optical detector for detecting reflected laser light; and a patient coil arrangement for mounting against a body of a patient;

a mounting arrangement for mounting the laser such that the delivered laser light passes to or though the patient coil arrangement; and a controller which is adapted to process the detected reflected laser light to detect the cardiac cycle and to generate a cardiac trigger signal for the control of the scanner.

In this example, the laser may not be aimed at a window of the patient coil (so no window is needed) but at the coil or coil-cover itself to detect vibrations of the measurement coil, which can subsequently be used for gated detection, and/or motion artefact reduction.

The invention also provides a computer program comprising computer program code means which is adapted, when said program is nm on a computer, to perform the method defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
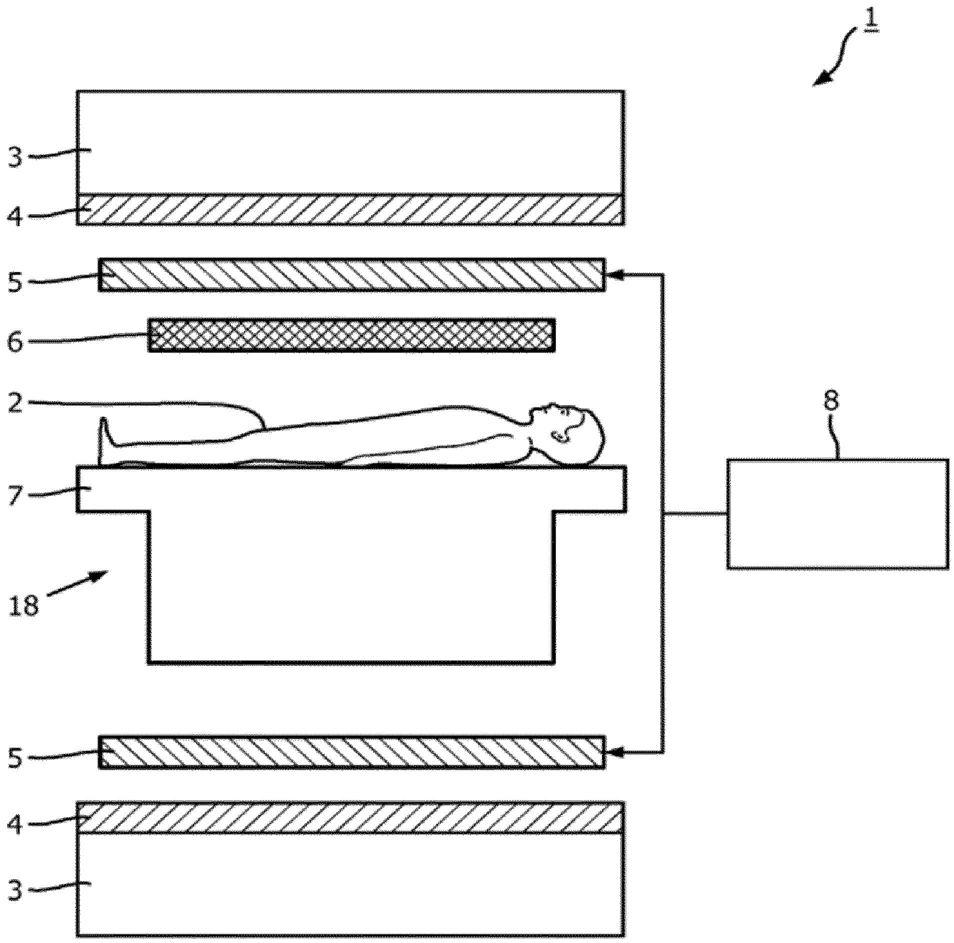
FIG. 1 shows in simplified schematic form an MRI system (scanner)

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system for providing a trigger signal for controlling the operation of a scanner. A laser speckle vibrometry system is used for vibration sensing. A patient coil arrangement is provided for mounting adjacent (e.g. fixing to) a body of a patient and it comprises at least one window enabling passage of the laser light of the optical system to the body of the patient. The detected reflected laser light (through the window) is processed to detect the cardiac cycle and to generate a cardiac trigger signal for the control of the scanner.

FIG. 1 shows in simplified schematic form an MRI system (scanner). The MRI system 1 is only shown with its most fundamental components, i.e. components which are of relevance for the present invention. In this respect, the MRI system 1 comprises a gradient coil 4 within the bore of the superconducting magnet 3 as well as RF transmit coils 5 and a RF receiver coil 6.

Local coils are applied to the patient within the MR bore, and these local coils will be referred to as the "patient coil". The patient coil may include multiple individual coil elements and the term "patient coil" should be understood accordingly. The patient coil typically functions as the RF receiver coil. The coil elements applied to the patient within the MR bore are for example multi-channel receivers. There have also been recent developments of a patient coil in the form of transceiver coils that also transmit the excitation signal.

In low field MRI systems, the severe constraints of local specific absorption rate are relaxed so that local transmit coils are an option. Thus, the patient coil can be a receive coil or a transmit/receive coil. It is basically the local coil applied to the patient no matter what function that coil is used for. There are also developments of wireless patient coils with system data communication using integrated 5G-like transceivers.

The patient coil is for example worn around the part of the body of the patient being imaged. For cardiac MRI, a patient coil is known in the form of a wearable vest around the torso of the patient, have an array of individual pick up coils, i.e. coil elements.

The RF transmit coils 5 emit RF pulses, which are supplied from a RF transmitter 8, and generate a radio frequency magnetic field within the bore of the superconducting magnet 3.

As is well known by one of ordinary skill in the art, by transmitting RF pulses which have an orthogonal polarization to the magnetic field generated by the superconducting magnet 3 and matching the Larmor frequency of the nucleons of interest, the spins of the nucleons can be excited and brought into phase, and a deflection of their net magnetization from the direction of the field of the superconducting magnet 3 is obtained so that a transversal component in relation to the longitudinal component of the net magnetization is generated.

After termination of the RF pulse, the relaxation process of the longitudinal and reversal components of the net magnetization begin until the net magnetization has returned to its equilibrium state. Magnetic resonance signals, which are generated by the precessing magnetization are detected by means of the RF receiver coil 6, i.e. the patient coil.

The received magnetic resonance signals are time-based amplitude signals, which are further Fourier transformed to frequency-based magnetic resonance spectrum signals and further processed for generating a magnetic resonance image of the nucleons of interest.

The RF transmitter 8 comprises an RF amplifier for generating RF pulses and for forwarding these RF pulses to the RF transmit coil 5 of the MRI system 1. Further, the RF transmitter 8 typically comprises a capacitor bank which is coupled to the RF amplifier, for storing electric energy and for providing the RF amplifier with a current for generating the RF pulses. A mains power supply is coupled to the capacitor bank 10, for generating a charging current for charging the capacitor bank with electric energy.

As discussed above, motion tracking may be used to trigger the operation of the scanner and thereby remove motion artefacts from the captured images. The invention uses a non-contact and unobtrusive monitoring of movement, in particular heart motion tracking, during the MRI scanning.

The invention for example makes use of motion tracking with laser speckle interferometry to create cardiac triggering similar to seismocardiography (SCG) based triggering. In particular, instead of traditional vector ECG, rPPG-sensor and video-based methods, the analysis of a laser speckle pattern on a patient's chest can be utilized for heart motion detection and optionally also for respiratory motion detection.

Figure 2:
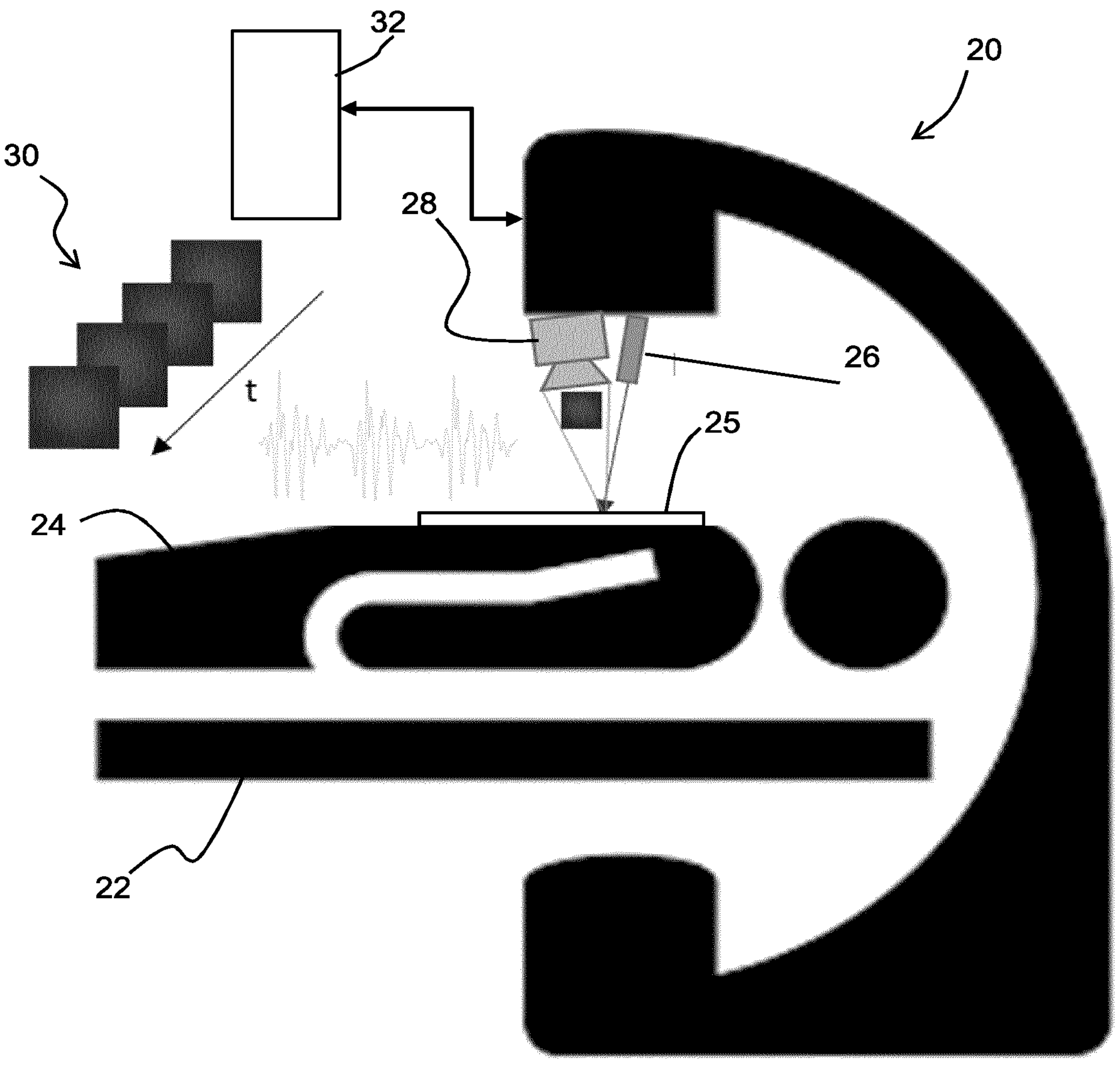
FIG. 2 shows an MRI scanner including an optical system for non-contact vibration sensing.

FIG. 2 shows an MRI scanner 20. The scanner comprises all of the components shown in FIG. 1 but these are not all represented in FIG. 2 for the sake of simplicity. FIG. 2 shows the patient support 22 and the patient 24 within the scanner bore. As explained further below, the scanner has a modified patient coil 25 to allow an unobstructed view of the patient's chest.

The scanner comprises a laser speckle vibrometry system for non-contact vibration sensing, using this unobstructed view of the patient's chest, comprising a laser 26 for delivering laser light through the patient coil 25 and an optical detector 28 for detecting reflected laser light.

A controller 32 processes the detected reflected laser light to detect the cardiac cycle and to generate a cardiac trigger signal for the control of the scanner. In particular, an optically detected speckle pattern is processed and filtered and a resulting ECG-like signal is provided to the MR-scanner e.g. for triggering. High-resolution (triggered) MR imaging is thus possible without additional on-body sensors or workflow impairment. The triggered sequence of images is represented as 30.

The optical system uses a defocused camera. The cardiac and respiration motion can be monitored from such an image using near real-time spatiotemporal processing, enabling accurate and contactless MRI triggering.

Laser speckle vibrometry is a method for studying the mechanical vibrations which are produced by cardiovascular and cardiorespiratory activity. LSV is sensitive to rotations and translations.

Figure 3:
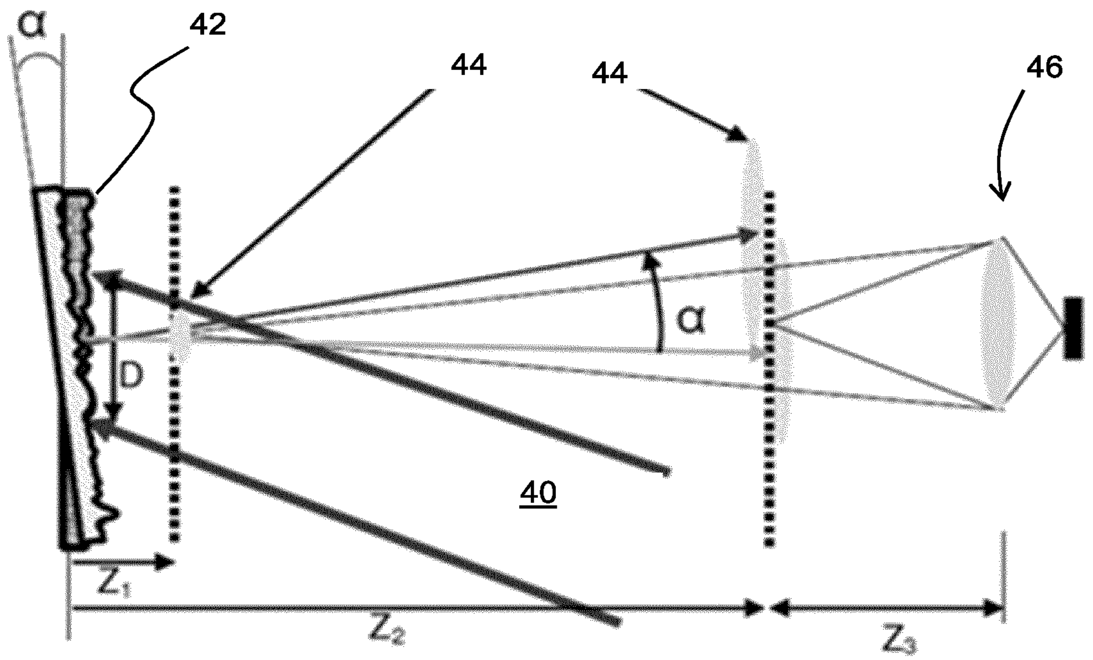
FIG. 3 shows a laser speckle vibrometry (LSV) system.

FIG. 3 shows a laser speckle vibrometry system. It comprises a laser signal 40 projected onto a diffusive object 42. The object moves as represented by the angular rotation a. Speckle patterns 44 are formed and captured by an imaging module 46.

Speckles are self-interfered random patterns. Speckle patterns are generated due to the roughness of the surface of the object when illuminated by a spot of laser beam.

When a spatially coherent beam is reflected from the object whose roughness generates a random phase distribution, in the far field the self-interfering, destructive and constructive speckle pattern is obtained.

In laser speckle vibrometry, the camera is not focused on the object, but rather focused on the far or close field such that the object itself is defocused. In this way, the movement of the object (its vibrations) causes a lateral shift of the speckles pattern.

Due to the defocusing, the movement of the object instead of constantly changing the speckle pattern creates a situation in which the same speckle pattern is visible but only moving or vibrating in the transversal plane. The magnification of the surface movement measured by the analysis of the dynamic speckle pattern can be controlled by the amount of defocus. The laser spot size also has an effect. A large laser spot gives rise to a small speckle pattern whereas a small laser spot gives rise to a large speckle pattern.

Experimental results obtained with a LSV setup have shown a close similarity between chest-worn accelerometers and the signal obtained after analysis of the dynamic speckle pattern on the chest.

Figure 4:
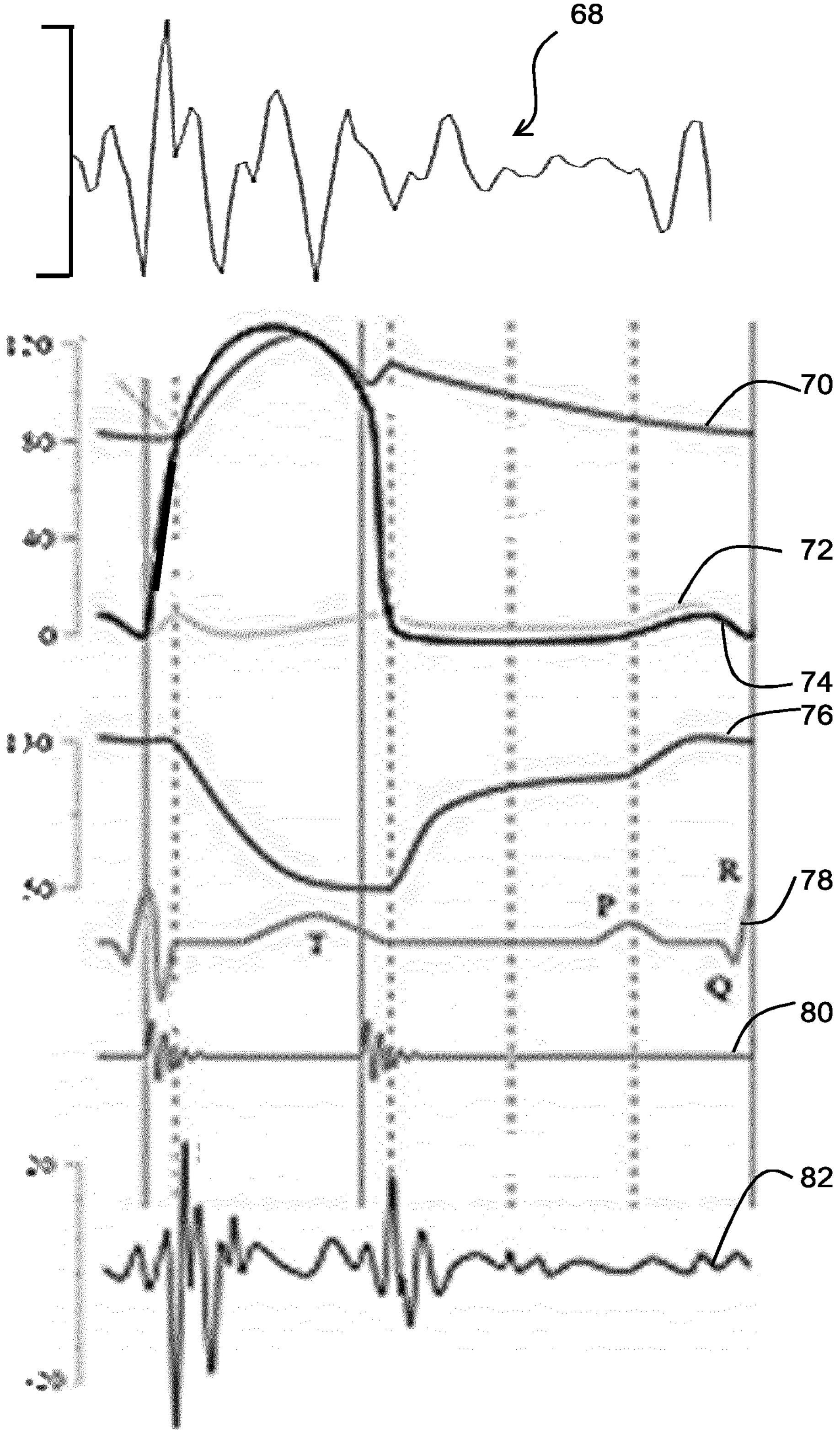
FIG. 4 shows the similarity between an SCG signal and a LSV signal.

FIG. 4 shows the similarity between an SCG signal and the LSV signal.

The signals represented are the LSV signal 68, the aortic pressure 70, the atrial pressure 72, the ventricular pressure 74, the ventricular volume 76, an ECG 78, a phonocardiogram 80 and a seismocardiogram 82. The first and most prominent feature of the SCG and LSV signals is related to the aortic opening.

It has been found that the measurement is rather insensitive to the angle of the laser and camera with respect to the vibrating surface, which allows many options for integration. In particular, the invention is based on performing the measurement through a window or multiple of the patient coil arrangement on the subject.

Compared to a PPG approach, the LSV signal is much more transient, and includes more cardiac timing information, e.g. related to the opening and closing of the aortic valve. This, combined with the low complexity processing and the absence of physiological time delays allows near real-time triggering with LSV.

Figure 5:
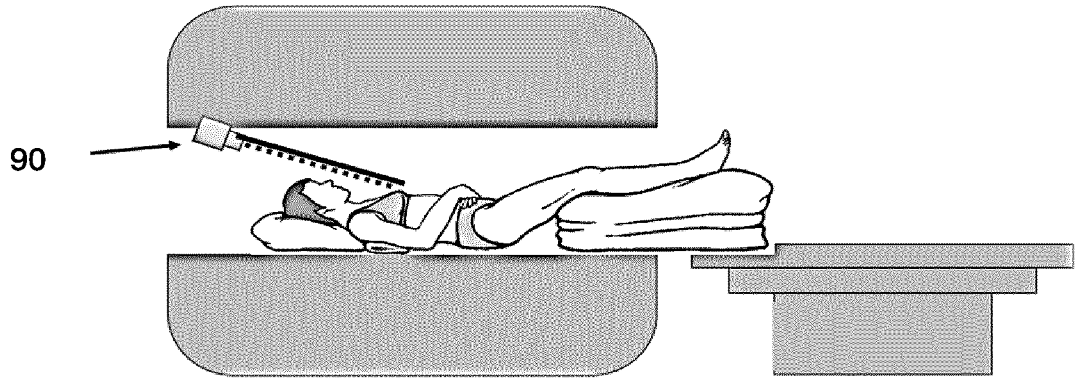
FIG. 5 shows a first implementation of the system shown generally in FIG. 2.

FIG. 5 shows a first implementation. The system comprises a (low-power) laser source and camera (shown as unit 90) mounted in (or close to) the bore and directed to the patient's chest. The camera is focused on a plane either before or beyond the point where the laser hits the chest, and detects a 'secondary' speckle produced by the reflected laser light off the patient's chest.

The camera detects the speckle pattern the laser produces on the patient's chest and the heart motion can then be deduced in near real-time from the video.

For this setup, an anterior patient coil is used with a window, so that there is a unobstructed optical path from the laser/camera to the chest. optical path.

Figure 6:
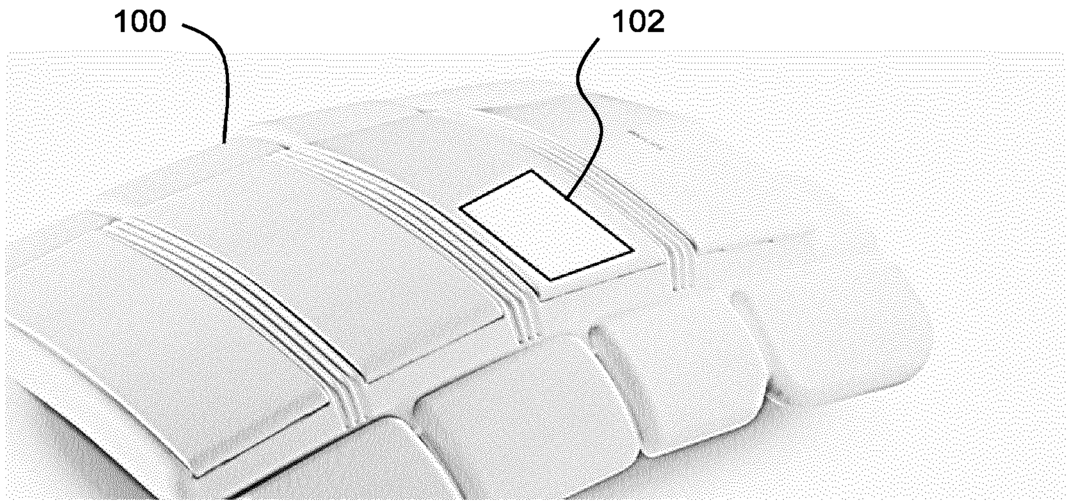
FIG. 6 shows a patient coil having a window.

FIG. 6 shows a patient coil 100 having a window 102 formed through one of the coil elements of the patient coil. The window 102 provides an optical opening through at least one of the coil elements within the anterior coil, e.g. using a plastic window in the middle of the coil element, where no coil conductors are positioned. A small mirror on top of the coil may also be used, that allows a suitable optical path to be formed.

Surface coils of the type shown in FIG. 6 are for example formed as arrays with multiple coil elements and hence multiple channels. For example, a whole body coil is known for whole body and peripheral vascular related imaging, with 108 channels covering the body, head and neck. For abdominal imaging, 12-24 channels are common.

Given the size of the desired field of view, this results in coil element diameters of around 10 cm, such as in the range 5 cm to 10 cm.

Recently developed arrays provide exceptional flexibility through drastically reduced amounts of supporting material, even allowing for open space in the center of each element. Opening sizes at the center of individual coil elements in the range 1 cm to 5 cm can be realized and these provide the space for the window 102.

There are various possible designs for the window.

A first option is to have the coil element with a fully free open recess in the center.

A second option is to provide the coil element with a covered optically transparent window. The cover enables easy disinfection.

A third option is to provide the coil element with an open window, but which can be opened and closed manually or automatically. The closure is again beneficial for disinfection, and for example to protect internal parts, such as integrated cameras, against dust and dirt.

The overall patient coil may have one or several windows. The use of multiple windows allows the window to be used which has best access to the most suitable area of the patient to be monitored for movement. A guiding system may be used to indicate how the patient coil should be positioned such that one of the windows is optimally located on a sensitive body area. Such a guiding system may comprise a 3D sensing device (camera, LIDAR) and a feedback system (audio, monitor) and a projection system to guide the patient or operator.

Figure 7:
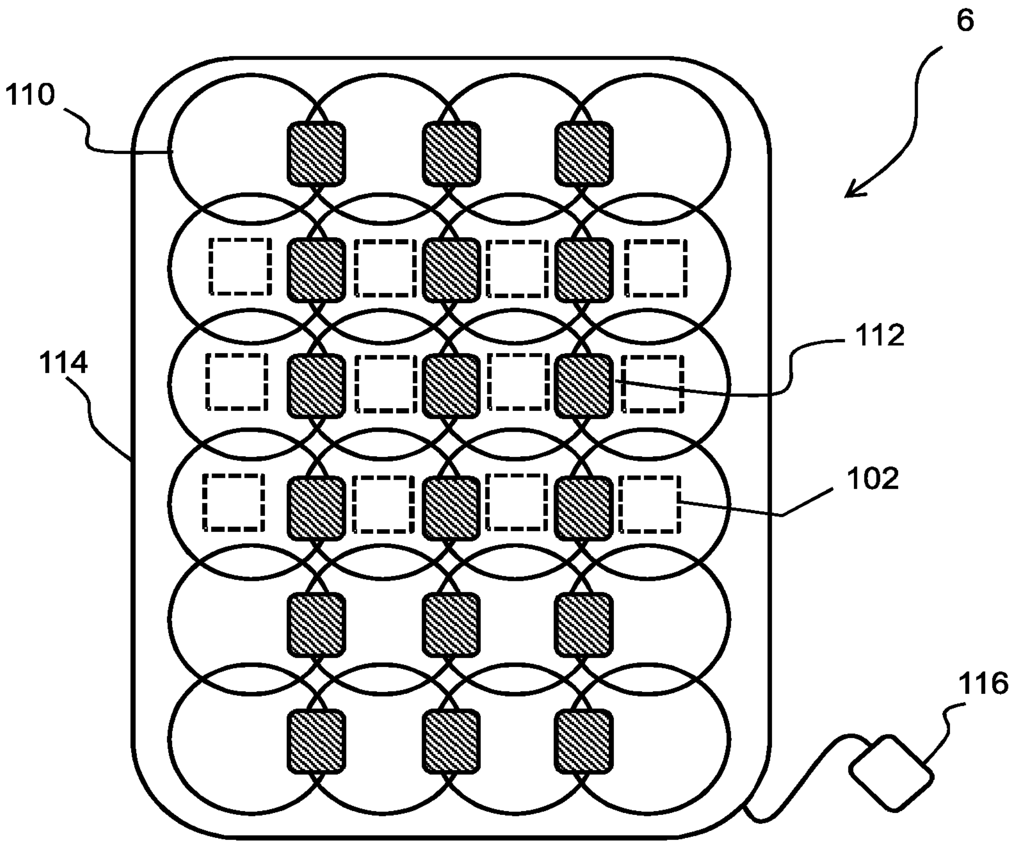
FIG. 7 shows an example of a patient coil design viewed from above.

FIG. 7 shows an example of the components of the patient coil 6. It comprises a flexible sheet 114 in which an array of conducting coil elements 110 is formed. The flexible sheet is for example formed as a foam material with a plastic cover. The stiffness of the coils low so that the overall patient coil may be fitted to the patient in the manner of a blanket. The patient coil may have integrated stiffening materials at certain locations, without hampering patient comfort, so that damping and latency of the detection system is reduced.

Electronics modules 112 are provided, for example including pre-amplifier circuits, for the conducting coil elements 110. Optical windows 102 are provided in a sub-set of the coil elements at locations where patient monitoring may be desired. A connector 116 is used to connect the patient coil 6 to the rest of the MRI system.

Figure 8:
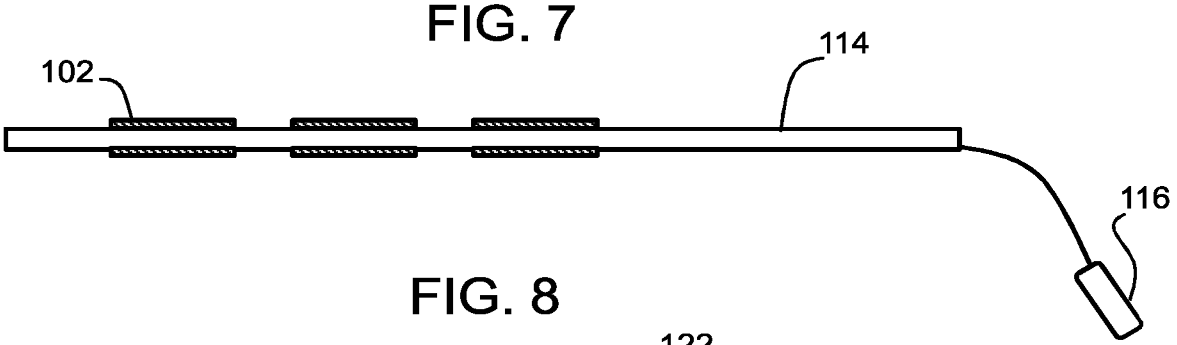
FIG. 8 show the patient coil viewed in cross section.

FIG. 8 shows a cross sectional view. The flexible sheet 114 for example has a fabric covering, and the optical window 102 is for example glued or sewn into the fabric covering. The optical window may also be removable or disposable so that it can be replaced if the optical transparency is reduced. Such a removable window may be fixed by sliding into position or by a zip fastening.

Figure 9:
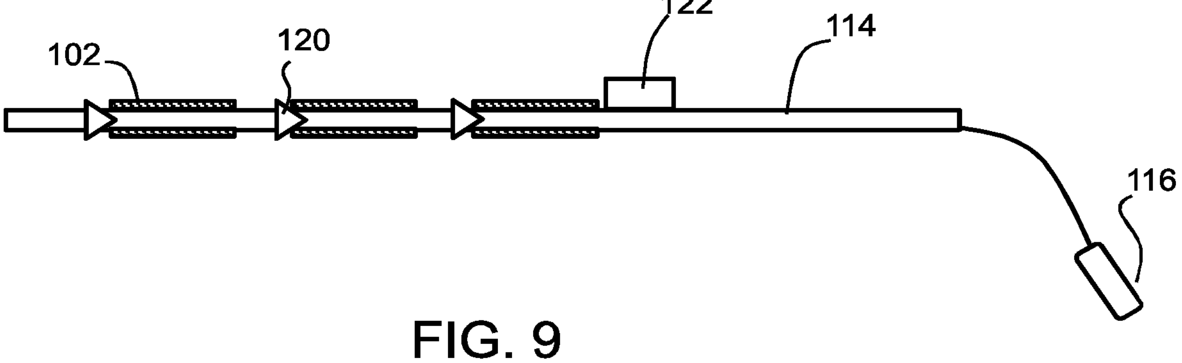
FIG. 9 show another example of the patient coil viewed in cross section.

FIG. 9 shows a modification to FIG. 8 showing light sources 120 integrated into the patient coil 6 to provide illumination of the optical window to provide better contrast for 3D sensing. The surround to the windows for example has an anti-reflection coating to prevent laser reflections.

This example also shows an optical marker 122 (there may be a set of such markers) for supporting automated positioning and to detect coil movement. For example, the patient bed or the patient can move during the scan and the optical windows can change position periodically due to the generally flexible nature of the patient coil. The marker or markers enable tracking so that recalibrations can be performed.

Figure 10:
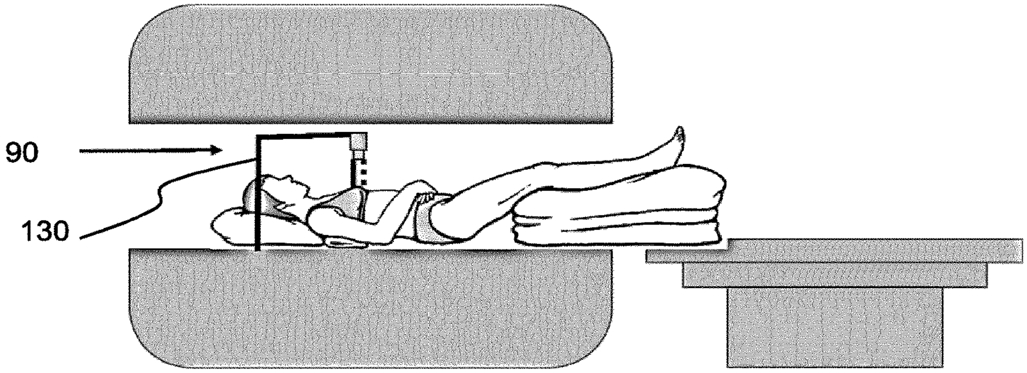
FIG. 10 shows a second implementation of the system shown generally in FIG. 2.

FIG. 10 shows a second implementation in which the camera and laser (again shown as unit 90) are mounted on an adjustable handle 130 which is fixed on one side of the patient bed for example next to the head rest.

An advantage of this set up is that it allows more flexibility. While the exact location of the anterior coil is dependent on the selected examination and may vary, the camera and laser module 90 can easily be located in a position such that an optimal view through the coil window and on to the patient's chest can be realized. Suitable handles, that are MR compatible and that can be fixed in arbitrary position are already well known and commercially available.

Figure 11:
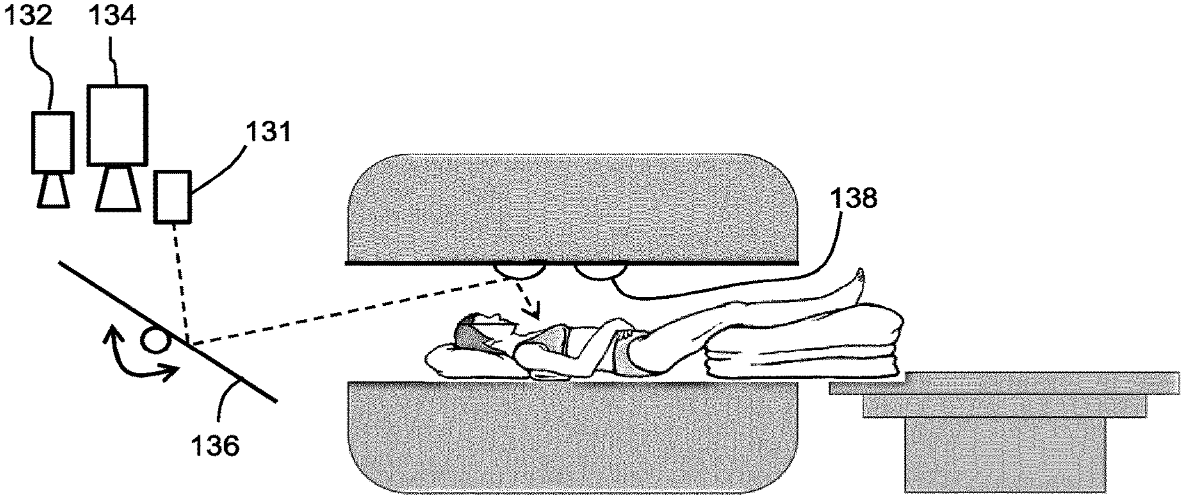
FIG. 11 shows a third implementation of the system shown generally in FIG. 2.

FIG. 11 shows a third implementation in which the laser 131 directs its output to a rotatable mirror 136 so that the laser beam direction can be adjusted to strike a concave mirror 138 mounted against the MRI coil at a desired location. It is then reflected to the window in the patient coil. The laser speckle vibrometry detector 134 is defocused, but there is also a focused camera 132 for tracking. The one or more convex mirrors may be used to cover a relatively large range of illumination, rather than multiple straight mirrors, each of which has only limited range.

The tracking camera 132 for example uses LIDAR or time of flight, and it means that if the patient bed has moved or the patient has changed its position (e.g. during breathing), a feedback tracking method may be used to track the position of the patient and to center the beam in the patent coil window.

Figure 12:
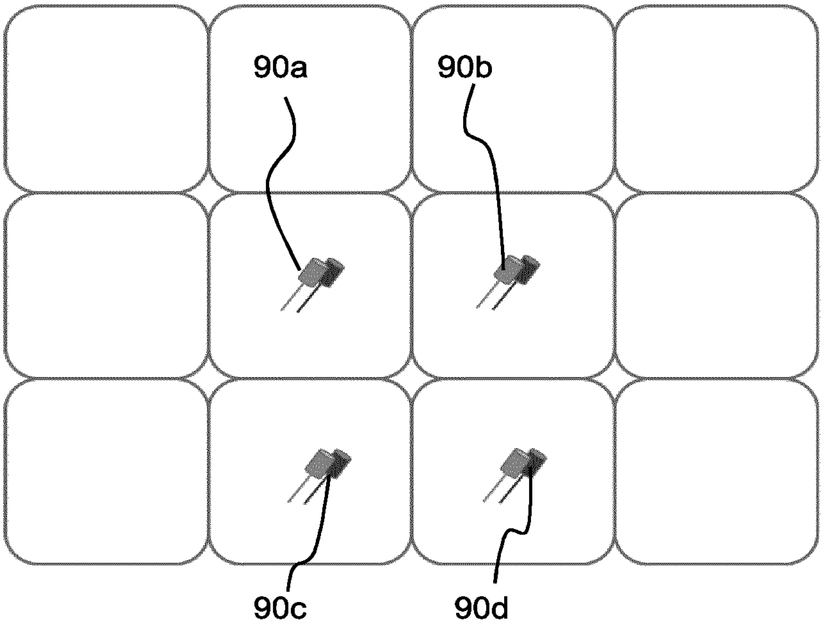
FIG. 12 shows that a plurality of laser and camera modules may be mounted directly into the coil structure.

FIG. 12 shows that a plurality of laser and camera modules 90*a*-90*d* may be mounted directly into the coil structure so that the window only need to be from the inside of the coil structure towards the patient, rather than all the way through the coil structure. Each module is integrated into a respective one of a set of individual coil elements of the patient coil. The modules are placed such that laser and camera are directed downward to the patient. Power and data connections to these modules can be provided by the coil and scanner infrastructure.

Since miniature cameras and suitable lasers exist, integration is possible since the coil connection can provide bias for all components as well as high data-rate connection to the scanner or host computer.

A coil support may then be provided in order to decouple the patient motion from the camera and laser module. Miniature cameras or LIDARS can also be integrated in a mattress or in the patient bed, with alignment through the window or windows of the patient coil. Patient motion may for example be detected and compensated using AI.

The overall system may for example be integrated into a bed or mattress by incorporating windows and the detection equipment into the bed or mattress. A structured layout of the mattress foam, integrating holes for windows, may be achieved without significantly impairing patient comfort.

In another example the optical system may be part of a belt which is mounted around the patient coil. Again, the patient motion would need to be decoupled from the camera and laser module, for example by having a patient coil support (so that the patient coil is decoupled from the movement of the patient).

When multiple camera and laser modules are used, a module may select the best signals resulting from the speckle patterns of different camera and laser modules.

Figure 13:
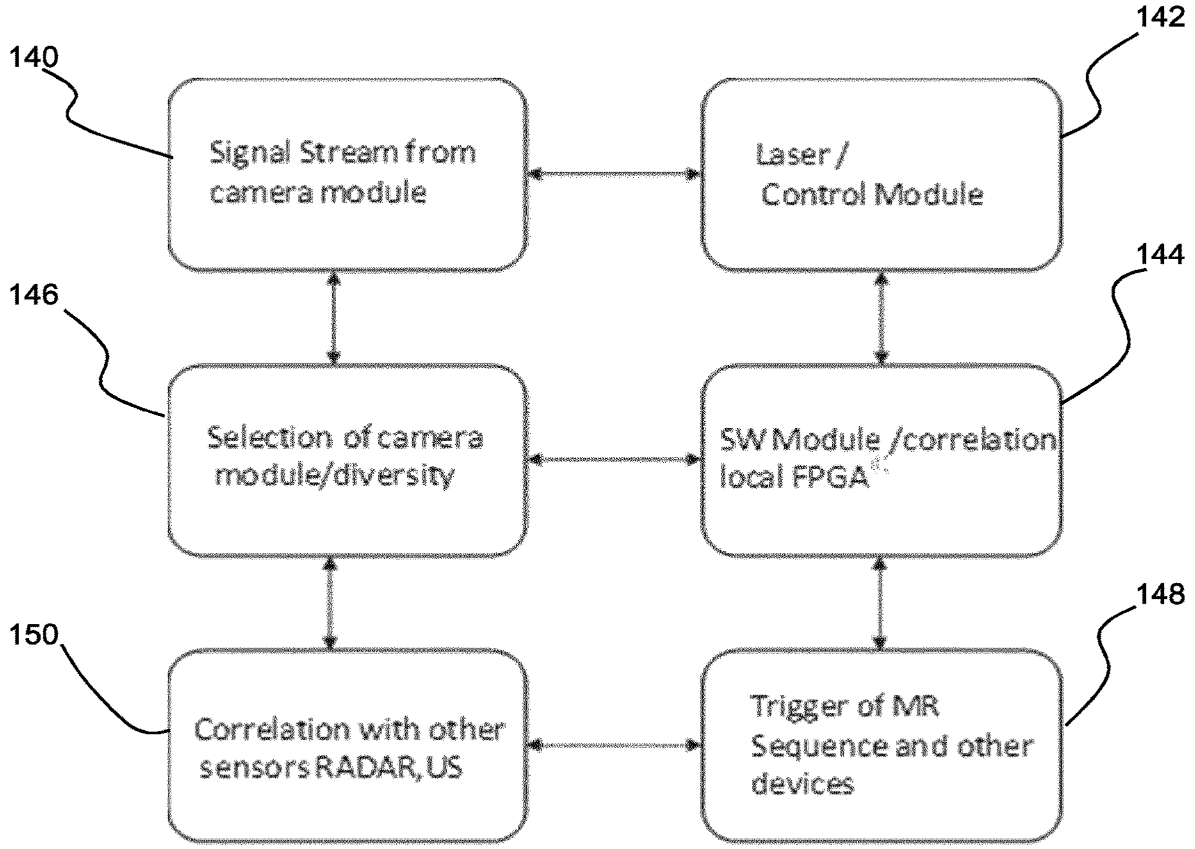
FIG. 13 shows a flow chart of the signal stream.
Figure 14:
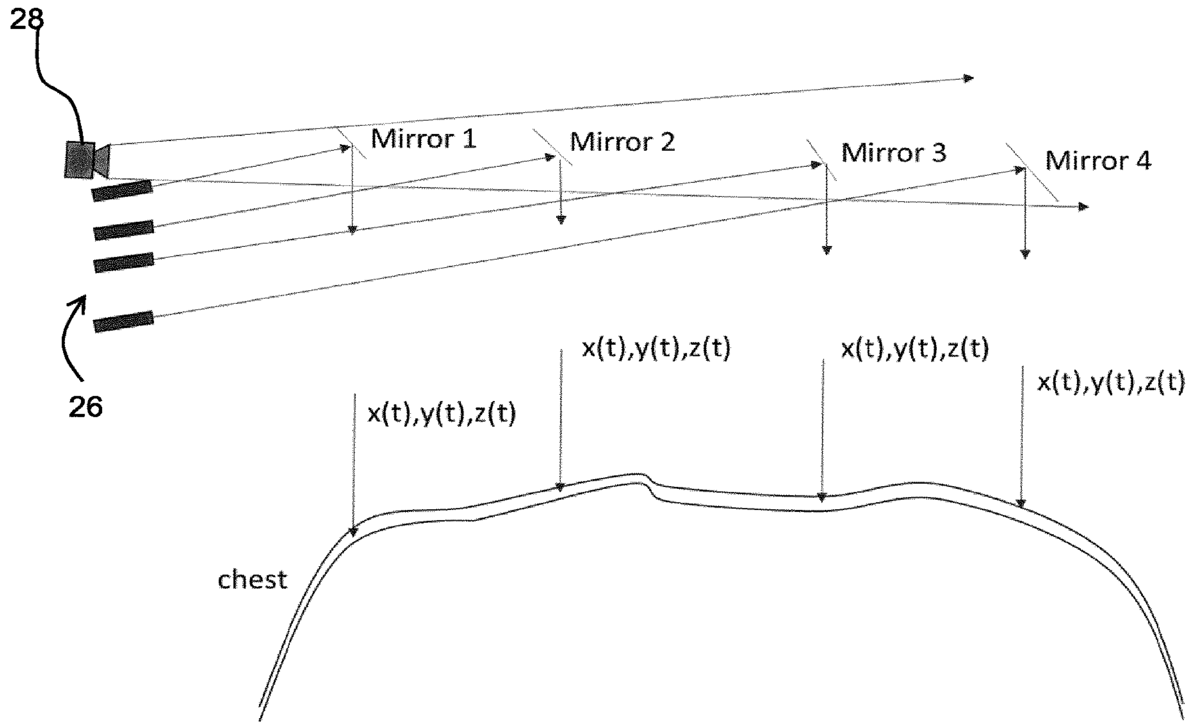
FIG. 14 shows that multiple lasers may be positioned at different locations on the chest.

FIG. 13 shows an example flow chart of the signal stream.

The signal stream from the camera is obtained in step 140, resulting from laser control in step 142. The output of the camera module is analyzed for example by a FPGA in step 144.

In step 146, a selection of the best camera signal is made. Then either improved trigger signals are generated in step 148 or the signals are combined with additional sensors like RADAR or ultrasound in step 150. For example, correlation of the signals or the outputs of one system are used to set a region of interest for the other device thus improving the overall signal quality.

Multiple lasers may be positioned at different locations on the chest, for example through different holes in the coil via small steerable/movable mirrors.

This approach is shown in FIG. 15, which shows a set of mirrors "Mirror 1" to "Mirror 4" each aligned with an associated laser 26 but using a shared camera 28. The speckle patterns are projected to different locations of the camera sensor, where each of the patterns can be evaluated for micro motions accordingly. The combination of the multi-spot measurements has the benefit of increasing the signal to noise ratio of the triggering signal.

The example above make use of one or more windows in the patient coil. In another arrangement, it is movement of the patient coil itself or the patient coil cover (since these may be fixed to the patient) which is detected. The delivered laser light then passes to (instead of through) the patient coil arrangement.

In an example, optimization of signal acquisition may be achieved by personalization of settings and a personalized system setup. In order to increase the sensitivity range, the camera and laser system may be customized to the individual breathing amplitude of the patient. The camera pointed to the patient's chest senses the amplitude of the chest movements (breathing amplitude).

Subsequently, using a feedback loop, the camera/laser system may then automatically re-adapt without any need for action on part of the operator. In particular, the amount of defocus can be controlled by the detected amplitude, such that the dynamic speckle pattern covers the entire image sensor for the best signal to noise ratio.

The invention is of interest for all imaging modalities but is of most interest for MRI due to rather long scans and exams and the need for trigger signals. The invention in particular addresses several shortcomings of the current approaches. Most importantly, no additional sensors have to be applied. Thus common workflow and patient throughput is not affected. Furthermore, sensor failure and misplacement (especially an issue with ECG placement) is avoided. The physiological effect (time delay) between the heart beat and measurement of the pulse rate or shape at distant locations from the heart is overcome since the measurement is carried out on the chest region of the patient, nulling any delays.

Compared to rPPG the measurement is not affected by skin perfusion or external factors such as temperature, and allows near real-time processing. Compared to rPPG, the signal from vibrometry also corresponds directly with motion and does not involve an unknown physiological delay associated with rPPG. Compared with rPPG-based vital signs camera measurements, there is no requirement on skin visibility; accurate measurements are possible through multiple layers of textile.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A system for providing a trigger signal for controlling the operation of a scanner, comprising:
- a laser speckle vibrometry system for non-contact vibration sensing, comprising a laser for delivering laser light, a defocused optical system, and an optical detector for detecting reflected laser light, wherein the defocused optical system is for defocusing the laser light at the distance of the surface of a body of a patient to be scanned; and
- a patient coil arrangement for mounting against the body of the patient; wherein the patient coil arrangement comprises at least one window enabling the passage of the laser light to the body of the patient;
- a mounting arrangement for mounting the laser such that the delivered laser light passes through the window of the patient coil arrangement; and
- a controller which is adapted to process the detected reflected laser light to detect the cardiac cycle and to generate a cardiac trigger signal for the control of the scanner.

2. The system of claim 1, wherein the laser is mounted remote from the patient coil and the output of the laser is directed to the window.

3. The system of claim 1, wherein the laser is mounted remote from the patient coil and the output of the laser is directed to the a mirror which is mounted at the window.

4. The system of claim 1, wherein the laser and optical detector are mounted on a handle which has an adjustable position relative to the body.

5. The system of claim 1, wherein the laser and optical detector are mounted on the patient coil arrangement.

6. The system of claim 5, further comprising a coil support for decoupling movement of the body from movement of the patient coil arrangement.

7. The system of claim 1, further comprising a tracking system for tracking movement of the patient coil arrangement and for adjusting the direction of the laser light to the at least one window in dependence on the tracked movement.

8. The system of claim 1, comprising a plurality of lasers and associated optical detectors, with different lasers directed to different locations of the body.

9. The system of claim 1, further comprising a calibration system for calibrating an amount of defocus of the optical detector based on detected chest movements.

10. The system of claim 1, wherein the system is for providing a trigger signal for controlling the operation of an MRI scanner.

11. An MRI scanner comprising:
- a patient support;
- a superconducting magnet;
- a gradient coil;
- an RF transmit coil; and
- the system of claim 1.

12. A method for providing a trigger signal for controlling the operation of a scanner, comprising:
- controlling a laser to deliver laser light through at least one window of a patient coil arrangement to the body of a patient using a defocused optical system, wherein the defocused optical system is for defocusing the laser light is defocused at the distance of the surface of the body of the patient;
- receiving a signal representing detected reflected laser light;
- processing the signal representing the detected reflected laser light thereby to implement laser speckle vibrometry to perform non-contact vibration sensing to detect the cardiac cycle; and
- generating a cardiac trigger signal for the control of the scanner.

13. A computer program comprising computer program code including executable instructions stored on a non-transitory computer readable medium which, when said program code is executed on a computer enables the computer to perform the method of claim 12.

* * * * *